United States Patent [19]
Susi

[11] Patent Number: 5,213,109
[45] Date of Patent: May 25, 1993

[54] AIRWAY ADAPTER FOR MONITORING CONSTITUENTS OF A PATIENT'S BREATH

[76] Inventor: Roger E. Susi, 5680 S. Lake Burkett La., Winter Park, Fla. 32792

[21] Appl. No.: 807,138

[22] Filed: Dec. 13, 1991

[51] Int. Cl.$^5$ .............................................. A61B 5/08
[52] U.S. Cl. .................................... 128/719; 73/23.3; 73/23.37
[58] Field of Search ............... 128/719, 716, 718, 767, 128/200.11, 205.27, 912, 914, 730, 725, 724, 720, 200.18, 200.23, 205.29, 207.14, 205.12, 204.17, 204.22, 204.23; 250/343, 344, 345, 347, 353; 73/23.3, 23.37; 422/84, 93

[56] References Cited

U.S. PATENT DOCUMENTS

| | | | |
|---|---|---|---|
| 4,403,514 | 9/1983 | Osborn | 128/725 |
| 4,549,553 | 10/1985 | Hochberg | 128/730 |
| 4,668,635 | 5/1987 | Forster | 250/343 |
| 5,607,492 | 11/1991 | Yeldeman et al. | 128/719 |

Primary Examiner—Kyle L. Howell
Assistant Examiner—Marianne Harley
Attorney, Agent, or Firm—Head & Johnson

[57] ABSTRACT

An apparatus for use in measuring the chemical constituents of a patient's breath, such as $CO_2$, $O_2$ or the like in the form of an airway adapter having opposed circular ends for installation in a patient's ventilation tubing, the adapter having an intermediate portion, a window formed in the intermediate portion of the type, such as of sapphire, to permit light of the required frequency to pass therethrough, and a mirror within the adapter immediate portion opposite of the window and arranged so that at least a portion of the patient's ventilation gases pass between the mirror and the window so that light may be directed through the window and received back therefrom as reflected from the mirror to permit an analysis of the absorption of light by the patient's breath for determination of the constituents of the patient's breath.

10 Claims, 1 Drawing Sheet

AIRWAY ADAPTER FOR MONITORING CONSTITUENTS OF A PATIENT'S BREATH

SUMMARY OF THE INVENTION

Monitoring the constituents of a patient's breath, such as end tidel, $CO_2$ ($E_tCO_2$) provides excellent data for a physician's use in evaluating the patient's body functions. For this purpose, airway adapters are inserted into the patient's ventilation tubing to provide a tap for airway gases. Light can be passed through the adapter and the absorption of light by gases in the patient's breath can be analyzed. A problem exists with presently used airway adapters in that they tend to become fogged by condensation of water vapors, flem or other liquids within the patient's breath.

$CO_2$ analysis can best be accomplished by utilizing infrared wavelength light. The best type of window for passage of infrared light through an airway adapter is made of sapphire. In the presently used air adapters two sapphire windows are used, opposite of each other, with the patient's breath, or at least a portion thereof, passing between the windows. Sapphire windows are expensive, making the adapter using two such windows an expensive item. One of the objects of this disclosure is to provide an improved airway adapter that utilizes only a single window.

A second object of this disclosure is to provide an airway adapter for monitoring chemical constituents of a patient's breath that has less propensity to become fogged by condensation, flem or other liquid components.

The airway adapter of this invention for use in measuring the chemical constituents of a patient's breath, such as $CO_2$, $O_2$ or the like, has a first end portion and a second end portion designed for installation in a patient's ventilation tubing.

A window is formed in the intermediate portion to permit light to pass readily therethrough, preferably formed of sapphire or other material that is highly translucent to infrared light.

A suitable reflective surface for the wavelengths of light required is positioned within the adapter intermediate portion opposite of the window and arranged so that at least a portion of the patient's ventilating gases pass between the mirror and the window. Light directed through the window is reflected by the mirror back through the window. The reflected light can then be analyzed to determine chemical constituents of the gas passing in the space between the window and the mirror, that is, to provide information as to the chemical constituents of the patient's breath.

This system utilizes only a single window and when the window is of the type that is of relatively high expense, such as a sapphire window, the cost of the airway adapter is substantially reduced by the use of a single rather than dual windows. The use of this reflective method has the additional advantage of providing twice the optical path per given chamber width versus a dual window method.

In the preferred arrangement, the airway adapter first and second ends are substantially circular in cross-section to permit easy installation in a patient's ventilation tubing. The intermediate portion is flat in cross-section with generally planar, spaced apart sidewalls and spaced apart end walls. The sidewalls are closer together than the diameter of the end portions, and the end walls are further apart than the diameter of the end portions. In the preferred arrangement, the cross-sectional area of the intermediate portion is not substantially less than the cross-sectional area of the adapter end portions.

A window is formed in one of the generally planar sidewalls, and a mirror is deposited or secured to the interior surface of the other sidewall. In this manner the spacing between the window and the mirror is substantially less than the diameter of the adapter end portions.

In another embodiment, the intermediate portion is divided into a smaller and a larger cross-sectionally dimensioned chamber. This is accomplished by the use of an inner wall within the intermediate chamber. The window and mirror are placed in the smaller chamber. The larger chamber of the intermediate portion provides the major flow path through the adapter.

In a most preferred embodiment, the airway adapter has a flat intermediate portion, as above described, and an inner wall divides this flat intermediate portion into a first smaller portion and a second larger portion by placement of the inner wall closer to one of the intermediate portion end walls. The window and mirror are positioned in the adapter intermediate portion smaller chamber. In addition, an opening is formed in the intermediate portion larger chamber, preferably in one of the generally planar sidewalls. The opening is provided with a semi-permeable membrane that can be used such as for the attachment of an $O_2$ sensor.

A more complete understanding of the invention can be obtained from the attached description of the preferred embodiments, taken in conjunction with the attached drawings.

DESCRIPTION OF THE DRAWINGS

FIG. 5 is shown partially cut away to show a portion of the interior of the adapter and shows the use of a filter in the smaller chamber.

DESCRIPTION OF THE PREFERRED EMBODIMENT

Figure 1:
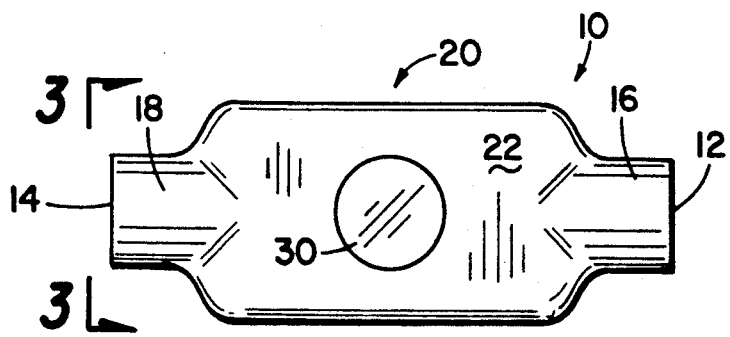
FIG. 1 is an elevational view of an airway adapter for use in measuring the chemical constituents of a patient's breath.
Figure 3:
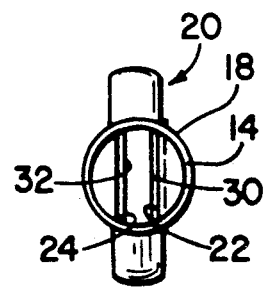
FIG. 3 is an end view taken along the line 3—3 of FIG. 1 showing the airway adapter.
Figure 2:
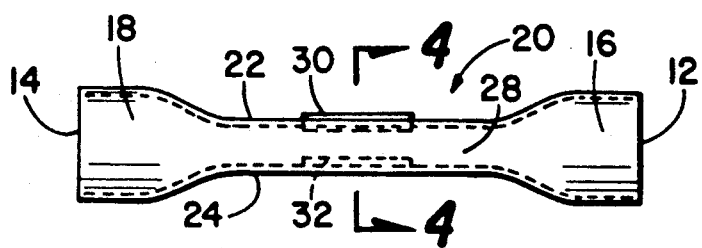
FIG. 2 is a top view of the airway adapter of FIG. 1.

Referring to the drawings and first to FIGS. 1-4, an embodiment of the invention is illustrated. These figures illustrate an apparatus for use in measuring the chemical constituents of a patient's breath, such as end tidel $CO_2$, $O_2$ or the like. The apparatus is in the form of an airway adapter, generally indicated by the numeral 10, that preferably is formed of plastic material. Adapter 10 has a first end 12, a second end 14, a first end portion 16 and a second end portion 18. In the typical arrangement, end portions 16 and 18 are circular in cross-sectional arrangement and thereby easily adapted for insertion into a patient's ventilation tubing.

The airway adapter includes a flat intermediate portion 20. As shown in the cross-sectional view of FIG. 4, the intermediate portion has: a first generally planar sidewall 22; a spaced apart generally planar second sidewall 24, the sidewalls 22 and 24 being generally parallel to each other; a first end wall 26 and a second end wall 28. The spacing between sidewalls 22 and 24 is less than the diameter of end portions 16 and 18, whereas the spacing between end walls 26 and 28 is greater than the diameter of end portions 16 and 18. In the preferred arrangement, the cross-sectional area of intermediate portion 20 is not substantially less than the cross-sectional area of end portions 16 and 18.

Formed in the first generally planar sidewall 22 is a window 30 that may be formed of any translucent material but preferably is of a material that is highly translucent to the specific frequency of light to be passed therethrough. $CO_2$ measurement is best accomplished utilizing infrared light, and, therefore, window 30 should be highly translucent to infrared. Sapphire is a material that is preferably used because of its high translucence to infrared.

Mounted on the interior surface of the second sidewall 24 is a reflective surface or mirror 32. The mirror is directly opposite of window 30.

Figure 4:
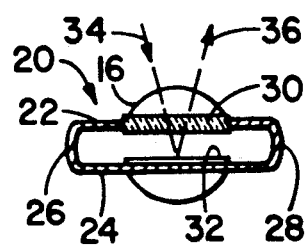
FIG. 4 is a cross-sectional view taken along the line 4—4 of FIG. 2 showing details of the internal arrangement of the airway adapter intermediate portion.

To provide an indication of $CO_2$ within the patient's breath passing through the airway adapter, light, indicated by the numeral 34 in FIG. 4, is directed through window 30. The light passes through the window and into the interior of the airway adapter intermediate portion 20. The light strikes mirror 32 and is reflected back through window 30, the reflected light being indicated by the numeral 36. The light passes through the patient's breath within the interior of the intermediate portion 20. As seen in FIG. 4, the length of the light path within the adapter is essentially twice the spacing between window 30 and mirror 32.

The reflected light 36 is analyzed to provide an indication of the chemical constituents of the patient's breath, such as $CO_2$, using techniques that are well known and which are not a part of this disclosure.

Figure 5:
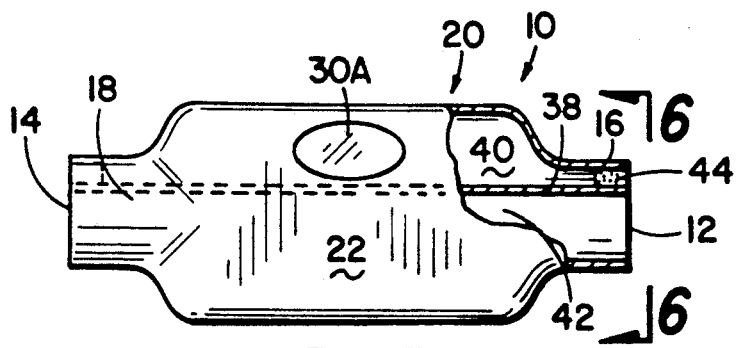
FIG. 5 is an elevational view of an alternate embodiment of the airway adapter having an internal wall dividing the intermediate portion into a smaller and a larger cross-sectionally dimensioned chamber.
Figure 6:
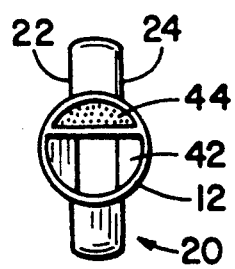
FIG. 6 is an end view of the embodiment of FIG. 5.

FIGS. 5 and 6 show an alternate embodiment. The exterior configuration of airway adapter 10 is the same as in FIGS. 1 and 2. However, in FIG. 5 an internal wall 38 divides the interior of the adapter intermediate portion 20 into a smaller cross-sectionally dimensioned chamber 40 and a larger chamber 42. The patient's breath passes through both chambers, however, larger chamber 42 provides a high flow chamber for patient ventilation. Window 30A is positioned within first sidewall 22 in the area thereof which encompasses smaller chamber 40 and in like manner, the mirror (not shown but directly behind window 30A) is attached to the interior surface of second sidewall 24, as illustrated with references to FIGS. 1-4, except that the mirror is positioned within smaller chamber 40.

The arrangement of FIGS. 5 and 6 has the advantage that the airway adapter can be oriented so that smaller chamber 40 is elevationally positioned above larger chamber 42. This minimizes the amount of flem condensed water vapor and other liquids in the patient's breath from obscuring the mirror and window that are in the smaller chamber 40 elevationally positioned above the larger chamber.

In FIGS. 5 and 6, a small filter 44 is placed in smaller chamber 42, and specifically in the first end portion 16, to further reduce the condensation and passage of liquid into smaller chamber 40. The use of a small filter 44 and the orientation available with the embodiment of FIG. 5 greatly reduces the possibility of the window and mirror becoming obscured by flem or other fluids within the patient's breath.

It should be noted that in the arrangement herein mirror 32 is completely internal of the airway adapter and thereby quickly reaches temperature equilibrium with the air within the adapter so that condensation on the mirror is substantially reduced.

Figure 7:
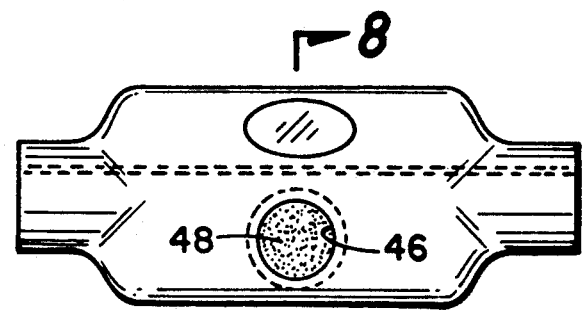
FIG. 7 is an elevational external view of still a different embodiment, similar to that of FIG. 5 but showing the provision of a semi-permeable membrane mounted within one of the sidewalls of the adapter intermediate portion providing means of attaching an instrument for measurement of $O_2$.
Figure 8:
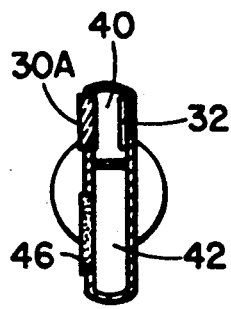
FIG. 8 is a cross-sectional view taken along the line 8—8 of FIG. 7 showing the details of the arrangement of this embodiment.

FIGS. 7 and 8 show a different embodiment of the arrangement of FIG. 5 in which an opening 46 is formed in the first sidewall 22 in a portion thereof communicating with the larger chamber 42. Positioned within opening 46 is a semi-permeable membrane 48. The membrane is preferably of the type permitting the passage of $O_2$ and permits the connection of instrumentation for measuring $O_2$ in the patient's breath, that is, opening 46 and membrane 48 provide a $O_2$ sensor port in the airway adapter 10.

Thus, it can be seen that the airway adapter as illustrated and described has advantages over airway adapters as currently employed.

The claims and the specification describe the invention presented and the terms that are employed in the claims draw their meaning from the use of such terms in the specifiction. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. Apparatus for use in measuring the chemical constituents of a patient's breath, comprising:
    an airway adapter having first and second end portions of generally circular configuration for installation in a patient's ventilation tubing and having an intermediate portion between the two ends, the intermediate portion being generally flat in cross-section with generally planar, spaced apart sidewalls and spaced apart end walls, the sidewalls being substantially closer together than the diameter of said end portions and said end walls being substantially further apart than the diameter of said end portions;
    a window formed in one of said generally planar sidewalls of said intermediate portion of the type to permit light to pass therethrough; and
    a mirror secured to the interior surface of the other of said generally planar sidewalls within the adapter intermediate portion, the mirror being opposite said window and arranged so that at least a portion of the patient's ventilation gases pass between the mirror and said window whereby light may be directed through said window and received back therefrom as reflected by said mirror to permit the reflected light to be analyzed, whereby the spacing between said window and said mirror is substantially less than the diameter of said end portions and wherein the cross-sectional area of said intermediate portion is at least about equal to the cross-sectional area of said end portions to provide no impedance to the air flow rate while permitting a minimal light travel path.

2. An apparatus according to claim 1 wherein said airway adapter has an internal wall which extends between said generally planar sidewalls and is positioned closer to one of said end walls than the other dividing said intermediate portion into smaller and larger cross-sectionally dimensioned chambers, and wherein said window and said mirror are in said smaller chamber, the larger chamber providing a major flow path through the adapter.

3. An apparatus according to claim 2 wherein said smaller chamber is elevationally positioned above said larger chamber.

4. An apparatus according to claim 2 including an opening formed in said intermediate portion larger chamber; and
a semi-permeable membrane closing said opening permitting means to measure selected gasses passing therethrough.

5. An apparatus according to claim 1 wherein said window is of sapphire.

6. Apparatus for use in measuring the chemical constituents of a patient's breath, comprising:
an airway adapter having first and second end portions for installation in a patient's ventilation tubing and having an intermediate portion between the two end portions, the intermediate portion having an internal wall dividing it into a larger and a smaller cross-sectionally dimensioned chamber;
a window formed in said intermediate portion smaller dimensioned chamber, the window serving to permit light to pass therethrough; and
a mirror within the adapter intermediate portion smaller dimensioned chamber and positioned opposite said window and arranged so that a portion of the patient's ventilation gases pass between the mirror and said window whereby light may be directed through said window and received back therefrom as reflected by said mirror to permit the reflected light to be analyzed, said intermediate portion larger chamber providing a major flow path through the adapter.

7. An apparatus according to claim 6 wherein said airway adapter first and second end portions are substantially circular in cross-section and wherein said intermediate portion is flat in cross-section with generally planar, spaced apart sidewalls and spaced apart end walls, the sidewalls being substantially closer together than the diameter of said end portions and said end walls being substantially further apart than the diameter of said end portions, said internal wall extending between said sidewalls and generally parallel to said end walls, said window being in one of said generally planar sidewalls and said mirror being secured to the interior surface of the other sidewall, wherein the spacing between said window and said mirror is substantially less than the diameter of said end portions.

8. An apparatus according to claim 6 wherein said window is of sapphire.

9. An apparatus according to claim 6 wherein said smaller chamber is elevationally positioned above said larger chamber.

10. An apparatus according to claim 6 including an opening formed in said intermediate portion larger chamber; and
a semi-permeable membrane closing said opening permitting means to measure selected gases passing therethrough.

* * * * *